(12) United States Patent
Peluso et al.

(10) Patent No.: US 8,075,544 B2
(45) Date of Patent: Dec. 13, 2011

(54) CONTAINERS AND METHODS FOR MANUFACTURING SAME

(75) Inventors: Francesco Peluso, Heverlee (BE); Tranaeus Anders, Shangai (CN); Dirk Faict, Assenede (BE); Patrick R. Balteau, Evelette (BE); Paul-Andre Gollier, Waterloo (BE); Jean-Luc Dewez, Bousval (BE); Eric J. Henaut, Arquennes (BE); Vincent Houwaert, Celles (BE); Philippe Lambert, Wezembeek-Oppem (BE)

(73) Assignee: Baxter International Inc., Deerfield, IL (US)

( * ) Notice: Subject to any disclaimer, the term of this patent is extended or adjusted under 35 U.S.C. 154(b) by 3 days.

(21) Appl. No.: 12/698,570

(22) Filed: Feb. 2, 2010

(65) Prior Publication Data

US 2010/0133278 A1    Jun. 3, 2010

Related U.S. Application Data

(62) Division of application No. 09/439,826, filed on Nov. 12, 1999, now Pat. No. 7,678,097.

(51) Int. Cl.
*A61B 19/00* (2006.01)

(52) U.S. Cl. ......... 604/410; 206/363; 383/210; 604/408
(58) Field of Classification Search ............... 604/403, 604/408–410, 416; 220/22, 62; 206/219, 206/221, 363–366; 383/35, 38, 40–42, 66, 383/94, 210, 210.1
See application file for complete search history.

(56) References Cited

U.S. PATENT DOCUMENTS

| | | | | |
|---|---|---|---|---|
| 3,836,425 A | * | 9/1974 | Whiting, Jr. | 428/213 |
| 4,479,989 A | * | 10/1984 | Mahal | 428/35.5 |
| 4,654,240 A | * | 3/1987 | Johnston | 206/524.6 |
| 4,686,125 A | * | 8/1987 | Johnston et al. | 383/116 |
| 5,023,119 A | * | 6/1991 | Yamakoshi | 428/35.2 |
| 5,577,369 A | * | 11/1996 | Becker et al. | 53/474 |
| 5,686,527 A | * | 11/1997 | Laurin et al. | 525/66 |
| 5,935,847 A | * | 8/1999 | Smith et al. | 435/297.5 |

* cited by examiner

*Primary Examiner* — Patricia Bianco
*Assistant Examiner* — Camtu Nguyen
(74) *Attorney, Agent, or Firm* — K&L Gates LLP

(57) ABSTRACT

A container is provided comprising a body defined, at least in part, by a film, the body including at least one side seal, at least two chambers separated, at least in part, by a peelable seal, and the film including a sealant layer having a bimodal thermal behavior such that the side seal is a permanent seal and the peelable seal can, at least in part, be separated.

6 Claims, 7 Drawing Sheets

CONTAINERS AND METHODS FOR MANUFACTURING SAME

CROSS-REFERENCE TO RELATED APPLICATIONS

This application is a divisional of U.S. patent application Ser. No. 09/439,826, filed Nov. 12, 1999 now U.S. Pat. No. 7,678,097, the entire specification of which is expressly incorporated herein by reference.

BACKGROUND OF THE INVENTION

The present invention relates generally to plastic films and containers made from same. More specifically, the present invention relates to containers for housing medical products and methods for manufacturing same.

It is known to house medical solutions in flexible containers constructed from plastic films. These containers can be used to house products such as parenteral, enteral, and dialysis solutions. Indeed, a great variety of different solutions can be housed and stored in such containers.

A number of issues are raised with respect to the containers for housing medical solutions, and the films that are used to construct such containers. These containers must be constructed so that they do not include harmful extractables that will leach out into the solution. This is especially important with respect to solutions such as parenteral solutions that are infused directly into the bloodstream of the patient.

Further, these containers must be able to stand up to certain rigors of use that other containers do not face due to environments in which they are used. Additionally, issues such as sterility and cleanliness, that may not be as critical with respect to containers used for non-infused solutions create manufacturing as well as product design issues for medical containers.

In fact, the products that are stored in the container themselves can create manufacturing, storage, and container design issues. There are a number of products that due to stability, compatibility, or other concerns must be stored in component parts, such as in separate containers, and admixed before use. This may be due to incompatibility of the products, for example, amino acids and dextrose solutions, or may be due to the fact that certain products must be maintained at different pHs from each other during sterilization or other processing, for example dextrose. Thus, it is known to provide multi-chambered containers. These containers include means by which the separate chambers can be placed in fluid communication with each other allowing the solutions from each of the separate chambers to be intermixed within the container and then administered to the patient.

Multi-chambered containers are much more desirable than storing the components in separate containers and then mixing same together. In part because the process of opening and mixing separate containers can compromise the sterility of the system. Further, the step of opening and mixing separate container creates a labor intense process. Accordingly, to deal with the disadvantages of separate containers, it is known to provide containers having an interior including two or more chambers. One way to create such a container is with a heat seal dividing the interior into two chambers. Such containers are disclosed, for example, in U.S. Pat. Nos. 4,396,488; 4,770,295; 3,950,158; 4,000,996; and 4,226,330.

For example, it is also known to use frangible valves across the heat seal to allow for the selective communication and mixing of the components stored in the separate chambers. See, for example, U.S. Pat. No. 4,396,488.

However, such structures—frangible valves—may not be desirable for a number of reasons including, inter alia, cost. An alternative to frangible valves is disclosed in U.S. Pat. Nos. 3,950,158; 4,000,996; and 4,226,330. In these patents, multiple chamber containers are disclosed with a line of weakness, such as a score line, which breaks upon the application of pressure.

It is also known to provide a selectively openable seal between two sheets of flexible thermoplastic material. U.S. Pat. No. 4,770,295 provides a seal line that is resistant to unintentional opening forces, but opens upon the application of a specific force. The container includes two sheets that form the exterior of the container and an inner diaphragm sheet between the outer sheets. A selectably openable seal is disposed between one of the outer sheets and the diaphragm sheet. A permanent line of securement is preferably included between the exterior sheet and the diaphragm sheet extending substantially parallel to and coextensive with the openable seal line.

In addition, tear tabs or tear strips for plastic packaging are also known such as shown in U.S. Pat. No. 2,991,000. These tear tabs can be used to provide access to the contents of the container. However, a disadvantage with these containers is that they involve the use of relatively complicated seal structures. U.S. Pat. No. 3,983,994 also discloses a seal broken by pulling upon tabs located outside the container.

Another issue that must be considered in constructing containers for the medical industry is that the solutions, and therefore the containers, often require sterilization after the manufacture of the container and/or introduction of the solution. Typically, the products are sterilized by steam sterilization or autoclaving. Autoclave sterilization can alter the thermal properties of the film used to form the container and the seal between the chambers of the container.

Of course, it is necessary in providing a multiple chamber container that the seal between the chambers is capable of withstanding external stresses encountered in normal handling, so that the seal is not prematurely opened. Such stresses include pressure that may be applied to one or more chambers from, for example, squeezing thereof incidental to packaging, or accidental dropping of the bag.

However, a difficulty in creating such a seal, using these types of materials is that the strength of the seal typically increases as a result of the heat applied during sterilization. As a result the seal may be too strong after the sterilization process making it difficult for the end user to separate or open the seal to combine the components within the chambers.

It is relevant to note that the end user of many of the medical solutions contemplated for use with the present invention is often the patient him or herself. This is particularly true in the case of the container being used to contain and administer solutions for peritoneal dialysis. Peritoneal dialysis is an alternative method to traditional hemodialysis by which a patient having end stage renal disease essentially treats him or herself by self-administering dialysis solutions a few times each day. However, patients undergoing dialysis tend to be elderly, often also diabetic, with poor eyesight and substantial weakness and diminished dexterity. Therefore, it is crucial that the force required to open the seal between chambers be carefully controlled to withstand normal handling and a certain amount of accidental jostling, yet not so great as to be difficult for such a patient to readily break when required to do so.

U.S. Pat. No. 5,577,369 discloses a flexible container including a plurality of internal compartments separated by a seal. At least the seal region is constructed from a film that comprises at least two layers, one of which is RF-responsive and the other layer, the inner layer, being non RF-responsive. The RF-responsive layer, in response to RF energy heats the non RF-responsive interior layer to form a peelable seal that is defined by a bonding between the non RF-responsive layers that define the interior of the container.

U.S. Pat. No. 5,209,347 discloses an internal tear seal container having at least two chambers. A selectively openable seal line is provided connecting two sheets of material. The selectively openable seal line is resistant to unintentional opening but opens upon the application of a specific force.

SUMMARY OF THE INVENTION

The present invention provides improved medical solution containers as well as methods for manufacturing same. The containers of the present invention include at least two chambers. The container is specifically designed for housing medical solutions although it can house other solutions and be used for other purposes.

To this end, in an embodiment, a container is provided by the present invention comprising a body defined, at least in part, by a film, the body including at least one permanent seal. The container includes at least two chambers separated, at least in part, by a peelable seal. The film includes a sealant layer exhibiting a bimodal thermal behavior such that the side seal is a permanent seal and the peelable seal can be opened.

In an embodiment, the sealant layer includes different polypropylene grades having different melting temperatures.

In an embodiment, the film includes an outer layer including polypropylene, a core layer including polyamide, and a sealant layer including polypropylene.

In an embodiment, the bimodal thermal behavior is such that a permanent seal is created at a temperature of at least 5° C. greater than the peelable seal.

In an embodiment, the sealant layer includes polypropylene and linear low density polyethylene.

In an embodiment, the container includes a first area defined, in part, by a peelable seal. The first area is designed to separate upon an application of a sufficient fluid pressure. In a further embodiment, the first area is coupled to a tube.

In another embodiment of the present invention, a container is provided including at least one peripheral permanent seal and defining at least two chambers having therebetween a peelable seal. The container is constructed, at least in part, from a film comprising an external layer that defines an outer surface of the container; the external layer includes polypropylene polymers. The film includes a core layer; and a sealant layer that defines, at least in part, an interior surface of the container, the peelable seal, and the permanent seal. The sealant layer exhibiting a bimodal thermal property.

In an embodiment, the core layer includes polyamide.

In an embodiment, the sealant layer includes linear low density polyethylene.

In an embodiment, the bimodal thermal behavior of the sealant layer is such that a permanent seal is created at a temperature of at least 5° C. greater than the temperature at which the peelable seal is created.

In an embodiment, the sealant layer includes styrene-ethylene-butylene-styrene (SEBS).

In an embodiment, the sealant layer includes: approximately 45% to, about 80% by weight polypropylene (PP); approximately 5% to about 20% by weight linear low density polyethylene (LLDPE); approximately 0% to about 25% by weight SEBS.

In a further embodiment, the sealant layer includes: approximately 45 to 80% by weight polypropylene; approximately 5% to 15% by weight linear low density polyethylene, approximately 0% to about 25% by weight SEBS; and approximately 0 to about 20% by weight of EVA.

In an embodiment, the sealant layer includes at least two different grades of polypropylene that have different melting points.

In a still further embodiment of the present invention, a container is provided including at least one permanent peripheral seal and defining at least two chambers having therebetween a peelable seal. The container is constructed, at least in part, from a film comprising: an external layer that defines an outer surface of the container, the external layer including polypropylene; a core layer; and a sealant layer that defines, at least in part, an interior surface of the container, the peelable seal, and the permanent seal. The sealant layer having a bimodal thermal property and including polypropylene, linear low density polyethylene, SEBS, and EVA.

In yet another embodiment of the present invention, a container is provided including at least one permanent side seal and defining at least two chambers having therebetween a peelable seal. The container is constructed, at least in part, from a film comprising: an external layer that defines an outer surface of the container, the external layer including polypropylene; a core layer; and a sealant layer that defines, at least in part, an interior surface of the container, the peelable seal, and the permanent seal. The sealant layer having a bimodal thermal property and including polypropylene having at least two grades having a different melting point.

It is an advantage of the present invention to provide an improved medical container for housing solutions.

A further advantage of the present invention is to provide a new film for use in constructing flexible medical containers.

Another advantage of the present invention is to provide an improved seal for creating multi-compartmented medical containers.

Still further an advantage of the present invention is to provide an improved medical container for housing two solutions in separate compartments that can be mixed together, prior to use, in the container.

Further, an advantage of the present invention is to provide an improved method for manufacturing medical containers.

Furthermore, an advantage of the present invention is to provide an improved method for making a peelable seal.

These and other features of the present invention as well as advantages thereof are set forth in and/or will be apparent from the following detailed description of the presently preferred embodiments and accompanying drawings.

DETAILED DESCRIPTION OF THE PRESENTLY PREFERRED EMBODIMENTS

The present invention relates generally to containers for housing medical solutions. As noted previously, however, the container of the present invention can be used for housing other types of products.

Figure 1:
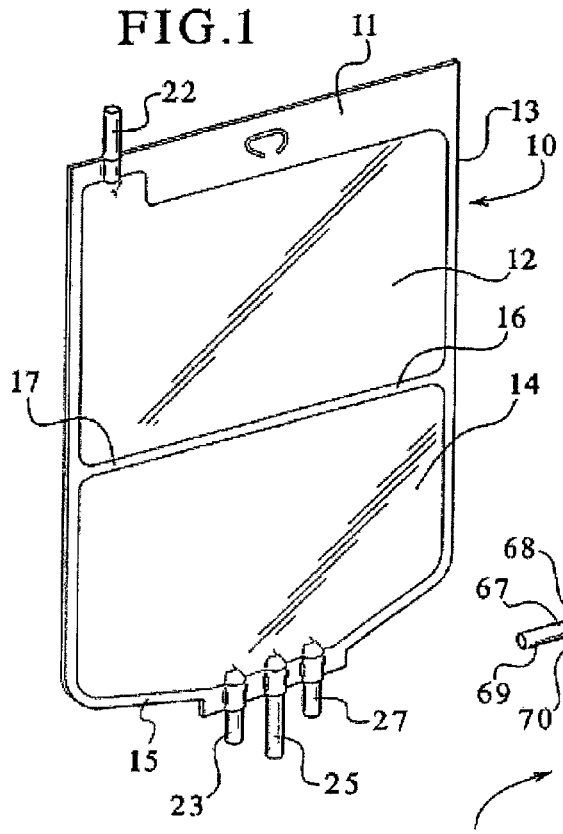
FIG. 1 illustrates a perspective view of the front side of an embodiment of a multi-chambered container of the present invention.

Referring now to FIG. 1, illustrated generally is an embodiment of a multi-chambered container 10 of the present invention. Although as illustrated the container includes two chambers 12 and 14, more than two chambers can be provided. The chambers 12 and 14 are designed for the separate storage of substances and/or solutions. A peelable seal 16 is provided between the chamber 12 and 14. Of course, if additional chambers are provided, additional peelable seals can be provided.

In the illustrated embodiment, the container 10 is formed from a flexible sheet of plastic. The container 10 may be formed from two sheets of film that are heat sealed along their edges (11, 13, 15, and 17 respectively). However, the container 10 can also be formed from a web of film folded over and sealed along three sides. Pursuant to the present invention, the container is formed from a multi-layer film discussed below.

In the illustrated embodiment, two sheets of film are used. The sheets are sealed about the periphery of the container 10 at edges 11, 13, 15, and 17. A peelable seal 16 is provided between the sheets of film to form the chambers 12 and 14.

In a preferred embodiment that is illustrated in FIG. 1 at an end of the container a tubular port 22 is provided. The tubular port 22 provides communication with the interior of chamber 12, but could be located at any appropriate location on container 10. The port 22 can include a suitable membrane covering which can be pierced by, for example, a cannula or a spike of an administration set. This allows additional substances to be aseptically added to chamber 12 or, once seal 16 is opened, to the container 10.

In the illustrated embodiment, disposed at a bottom end of the container 10 are three tubular ports 23, 25, and 27 which communicate with the interior of chamber 14. These ports allow fluid to be added to the chamber 14, or, once seal 16 is opened, to container 10 or dispersed to a patient therefrom. The ports 23, 25, and 27 can also include a membrane (not shown) that is pierced by, for example, the cannula or spike of an administration act.

It will be appreciated that ports such as 22 and 23 for filling the container 10 are not a requirement of the invention. Depending on the method employed to manufacture the containers, fill ports may not be necessary at all. For example, if the containers are to be manufactured from a continuous roll of plastic film, the film could be folded lengthwise, a first permanent seal created, the first compartment filled with solution, then a peelable seal created, a second compartment filled, a permanent seal created, and so on.

Pursuant to the present invention, a novel peelable seal 16 is provided. The container 10 and thus the peelable seal 16 is provided by utilizing films that include a novel sealant layer. The sealant layer allows both a peelable and permanent seal to be created. Thus, the permanent side seals 11, 13, 15, and 17 as well as the peelable seal 16 can be created from the same layer of film.

Figure 2:
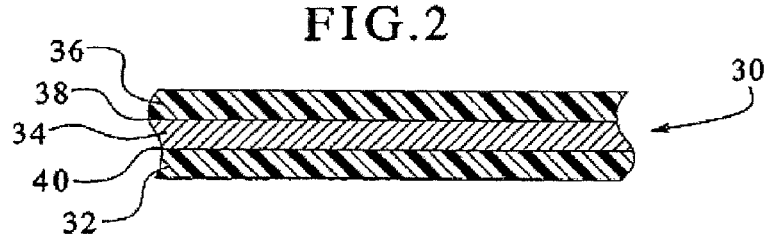
FIG. 2 illustrates a cross sectional view of an embodiment of the film of the present invention.

Referring to FIG. 2, an embodiment of the film 30 of the present invention is illustrated. The film 30 is illustrated in cross-section and includes at least three layers 32, 34 and 36. Layer 36 defines an exterior of the container 10, layer 34 defines a core layer and layer 32 defines the sealant layer. In the illustrated embodiment, the layers are secured together by tie layers 38 and 40.

The sealant layer 32 provides a layer having bimodal thermal behavior. In an embodiment, the sealant layer 32 comprises a composition that is made from the same material but different grades of material. In this regard, in an embodiment, the sealant layer 32 is a blend of different polypropylene grades having different melting temperatures due to their tacticity differences, or high ethylene random copolymer contest. For example, in an embodiment, high crystalline polypropylene polymers are used. High crystalline polypropylene polymers have a high melting temperature; preferably the melting temperature is above a 140° C. Additionally, these polymers have a narrow melting range.

Preferably, additionally the sealant layer 32 includes a more amorphous polypropylene with a melting temperature lower than 130° C. This lower melting point could, for example, be due to this second grade of polypropylene being more amorphous/less crystalline in character than the first grade of polypropylene grade in layer 32.

Using such materials, a peelable seal 16 can be made by melting the two opposing sealant layers 32 of the container 10 together whenever a peelable seal is desired at a temperature of for example between approximately 125° C. and 129° C. A permanent seal can be created by melting the two sealant layers 32 together at a temperature of above 135° C. Thus, the same sealant layer 32 can create both the permanent side seals and the peelable seals by merely forming each seal within a different temperature range. A variety of different sealing techniques can be used to make such seals including heat sealing, impulse sealing, and sonic sealing.

In this embodiment of the sealant layer 32, the peelable seal 16 is created due to a fusion of only the more amorphous low melting temperature polypropylene contained in the opposing sealant, side layer 32. Only these polymers participate in the resultant adhesion. By varying the composition of the sealant layer 32, one should be able to determine the adhesion level in the preferable range.

Figure 3:
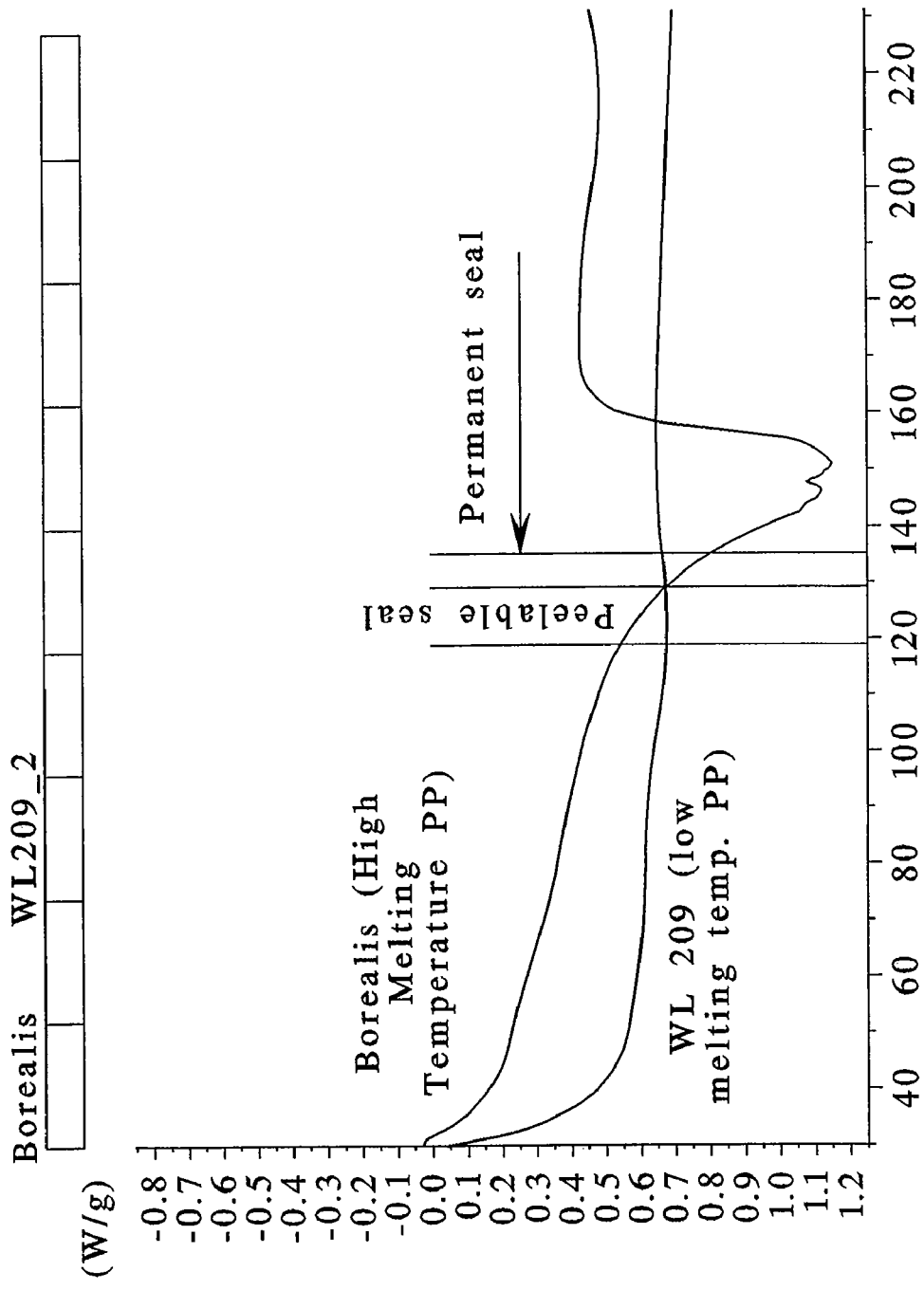
FIG. 3 provides a digital scanning calorimetry thermogram illustrating the seal strength versus sealing temperature of the sealant layer of an embodiment of the film of the present invention.

Referring to FIG. 3, a digital scanning calorimetry thermogram is illustrated. This thermogram demonstrates the bimodal behavior of materials of the present invention. The materials were measured by a commercial digital scanning colorimeter available from Mettler under the designation DSC 12E. In measuring the material, the material was submitted to a first heating cycle, from 30° C. to 220° C. at 20° C./min, cooled down to 30° C. at 10° C./min, and finally the measurement was carried out in a third heating step from 30° C. to 250° C. at 20° C./min. The heat flow is measured by comparison with a reference.

The embodiment of the film illustrated in FIG. 2 includes an outer layer 36 that comprises polypropylene. A tie layer 38 is located between the outer layer 36 and the core layer 34. The tie layer 38 may be polypropylene grafted maleic anhydride. The core layer 34 may be polyamide and preferably polyamide 6. This core layer 34 is then secured to the sealant layer 32 preferably utilizing another tie layer 40 of polypropylene grafted maleic anhydride.

Preferably, the outer layer 36 has a higher melting temperature than the internal layers of the film 30 in order to avoid adhesion during the sterilization process. This also prevents adhesion of the sealing die to the outer layer should heat seal dies be used to create the seals.

The core layer 34 of the film 30 should provide good mechanical and diffusion properties. The core layer 34 should maintain these properties even at temperatures up to 200° C., which is much greater than the sealing temperatures.

Figure 4:
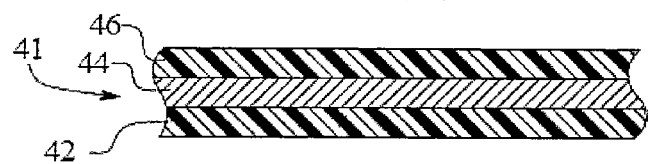
FIG. 4 illustrates a cross sectional view of another embodiment of the film of the present invention.

Referring now to FIG. 4, another embodiment of the film 41 is illustrated. The film 41 is illustrated in cross-section and includes at least three layers 42, 44 and 46. Layer 46 defines an exterior of the container 10, layer 44 defines a core layer and layer 42 defines the sealant layer. In this embodiment, the sealant layer 42 comprises polypropylene and linear low density polyethylene. In a preferred embodiment, the layer 42 comprises approximately 70% by weight polypropylene (PP). Polypropylene is a semi-crystalline polyolefin with a melting point between 126° C. and 170° C. (depending on the crystallinity of the material). It is most desirable that the polypropylene has a continuous phase, therefore, in a preferred embodiment the concentration should be at least approximately 60% by weight.

The sealant layer 42 also preferably includes linear low density polyethylene. Preferably in an embodiment, the sealant layer 42 comprises approximately 10% linear low density polyethylene (LLDPE) by weight dispersed in the polypropylene matrix. The linear low density polyethylene is a semi-crystalline polyolefin with a melting point between approximately 90° and 130° C. It could be used in a concentration ranging from between approximately 5 and 15% by weight.

Linear low density polyethylene in the sealant layer 42 plays two roles. It has a lower melting point than polypropylene and so it increases the bimodal thermal behavior of the blend. Also the highly amorphous character of linear low density polyethylene increases the mobility and compatibility of the dispersed phase, producing a better blend.

In an embodiment, the sealant layer also includes approximately 20% by weight styrene-ethylene-butylene-styrene (SEBS). SEBS is a triblock copolymer. In this regard, it comprises polystyrene block/ethylene-butylene copolymer block/polystyrene block. Ethylene-butylene is an elastomer. The complete triblock acts as a thermoplastic elastomer with a softening temperature at about 100° C. It should be the second dispersed phase, with concentrations between approximately 5 to about 20% by weight. The emulsion character of this triblock copolymer produces a low mobility even at temperatures above the softening point.

It should be noted in the above embodiment that ultra low density polyethylene (ULDPE) can be used in the same concentration as a replacement either in whole or in part for linear low density polyethylene and ethylene vinyl acetate could be added to improve scalability properties.

Figure 5A:
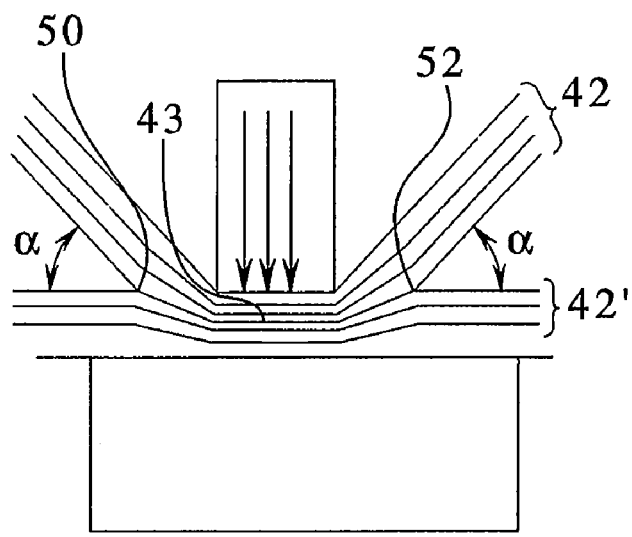
FIGS. 5(a) and 5(b) respectively illustrate an embodiment of a method of manufacturing a peelable seal and a permanent seal using an embodiment of the film of the present invention.
Figure 5B:
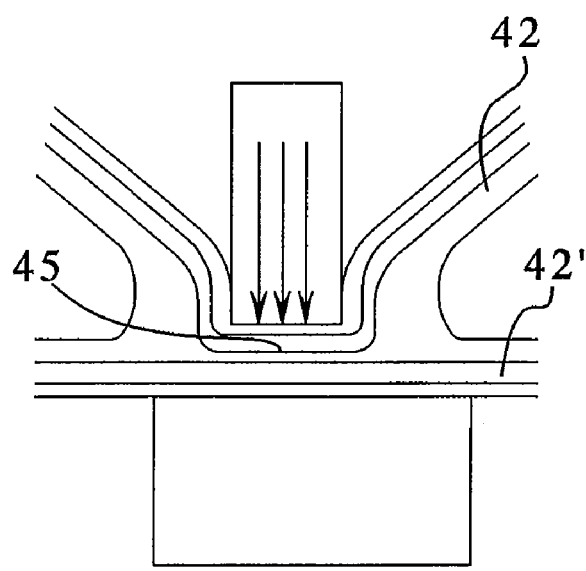

A principal of this embodiment of the peelable seal is that at low seal temperature (i.e., peel seal temperature) the sealant layer 42 behaves as a solid. Referring to FIGS. 5(a) and 5(b), the sealing of two sealant layers 42 and 42' together is illustrated. Specifically a peelable seal 43 and a permanent seal 45 are illustrated as being produced.

Referring specifically to FIG. 5(a), when the sealant layers 42 and 42' are heated only the dispersed phase is liquid. Therefore, the adhesion occurs just at those points making bridges 50 and 52 between the seal 43 of two layers of film 42 and 42'. The peelable seal's 43 strength is proportional to the number of those bridges. So the peelable seal's 43 strength is governed not only by the composition of the sealant layer 42 and 42', but also by the microstructure and so by the thermal and mechanical history of the matured. Furthermore, because sterilization is conducted at a low temperature (e.g. approximately 120° C.) the sealant layer 42 and 42' are solid, there is no viscous flow during the sterilization process reducing both intermixing and formation of the sealing bead.

Referring to FIG. 5(b), at higher temperatures, the sealant layers 42 and 42' each behave as viscous fluid leading to strong intermixing and formation of a sealing bead. This produces a permanent seal 45.

The sealant layer 42 provides a real bimodal system, with a plateau zone of peel sealability between approximately 110° C. to about 125° C. and a second plateau of permanent sealability. The linear low density polyethylene (highly amorphous) plays the role of a plasticizer and maybe a compatibilizer.

By way of example, a not limitation, examples of the present invention and testing thereof will now be given.

EXAMPLE No. 1

In this example, the sealant layer comprised:
approximately 45 to about 54% PP,
approximately 18 to about 27% SEBS,
approximately 9 to about 14% EVA,
approximately 4.5 to about 9% Parafinic oil,
approximately 9.8% LLDPE, and
approximately 2% ABPP.

Figure 6:
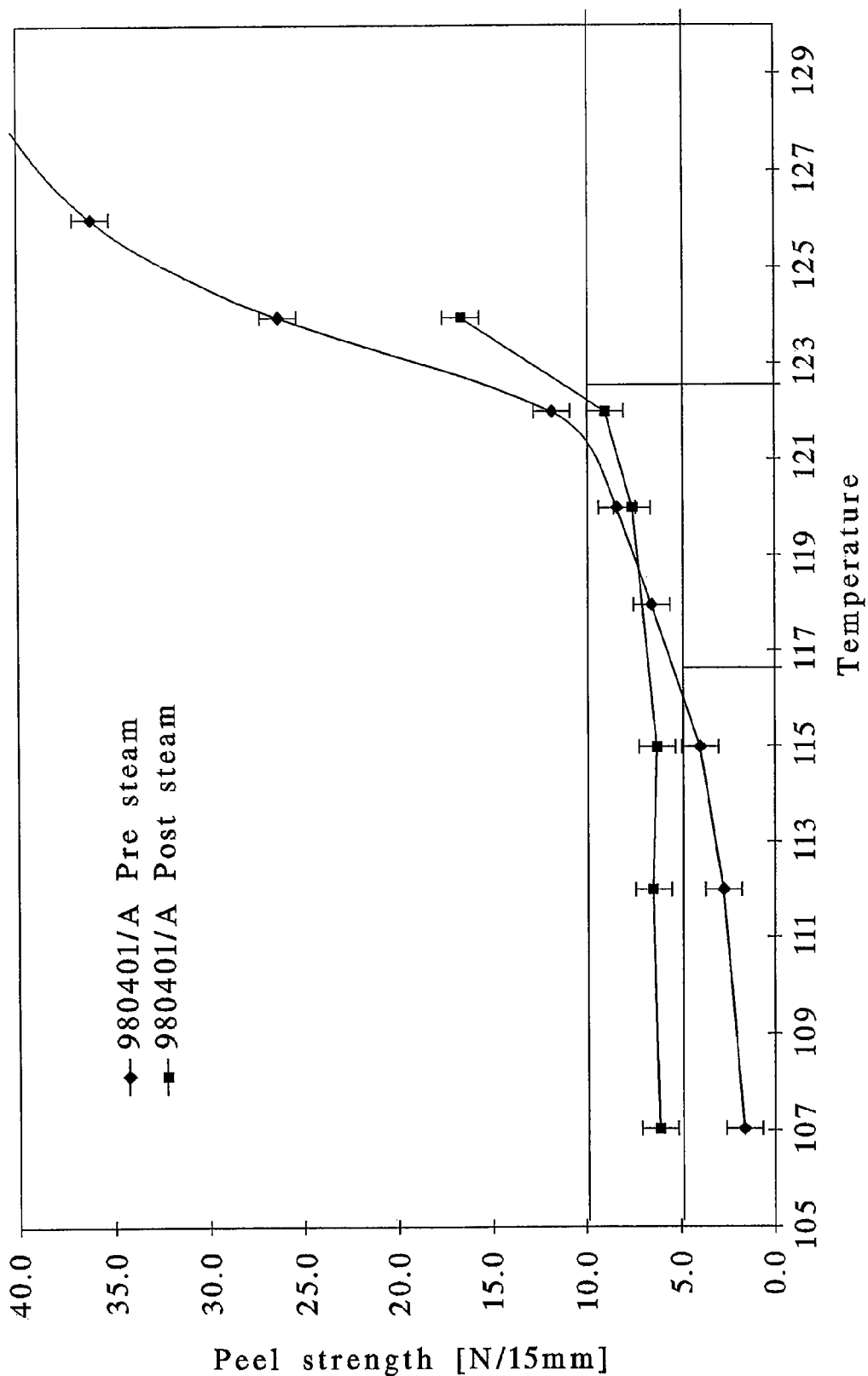
FIG. 6 illustrates graphically peel strength versus temperature of an embodiment of the seal layer of the present invention.

FIG. 6 illustrates graphically peel strength versus temperature for a sealant layer constructed pursuant to the above formulation. The seal was done on a thermal sealer with a pressure of 2 MPa for a 3 second welding time. The seals were 200 mm long and 4 mm wide. The strength measurements were performed on an Instron tensile machine on 15 mm wide strips cut perpendicular to the seal.

EXAMPLE No. 2

In this example, the sealant layer comprised:
65% PP co-ethylene random (4% ethylene), and
35% syndiotactic PP.

Figure 7:
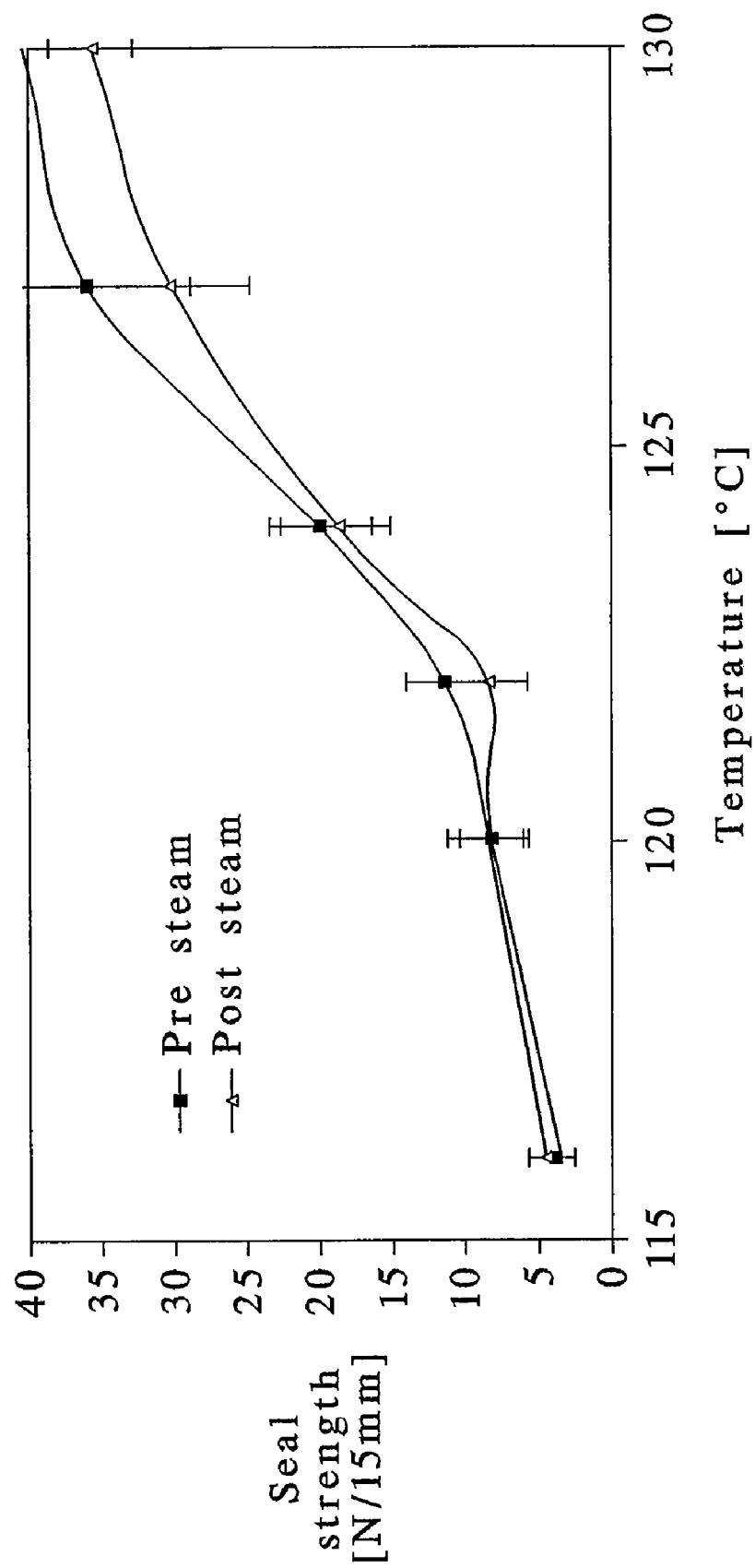
FIG. 7 illustrates graphically peel strength versus temperature of an embodiment of the seal layer of the present invention.

FIG. 7 illustrates graphically peel strength versus temperature for a sealant layer constructed pursuant to the above formulation. The seal was done on a thermal sealer with a pressure of 2 MPa for a 3 second welding time. The seals were 200 mm long and 4 mm wide. The strength measurements were performed on an Instron tensile machine on 15 mm wide strips cut perpendicular to the seal.

EXAMPLE No. 3

In this example, the sealant layer comprised:
60% PP co-ethylene random,
25% SEBS, and
15% LLDPE.

Figure 8:
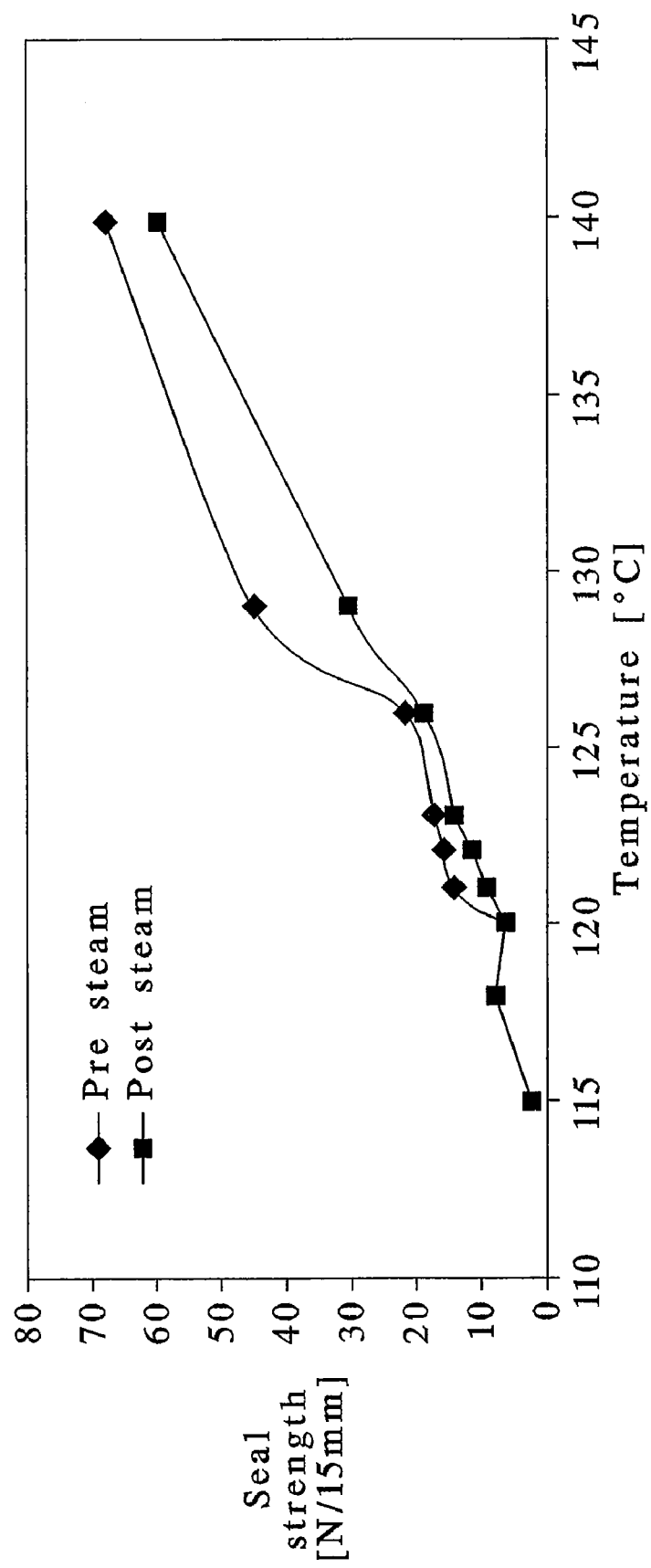
FIG. 8 illustrates graphically peel strength versus temperature of an embodiment of the seal layer of the present invention.

FIG. 8 illustrates graphically the seal strength. The seal was done on a thermal sealer with a pressure of 2 MPa for a 3 second welding time. The seals were 200 mm long and 4 mm wide. The strength measurements were performed on an Instron tensile machine on 15 mm wide strips cut perpendicular to the seal.

EXAMPLE No. 4

In this example, the sealant layer comprised:
60% PP,
20% SEBS,
10% EVA, and
10% LLDPE.

Figure 9:
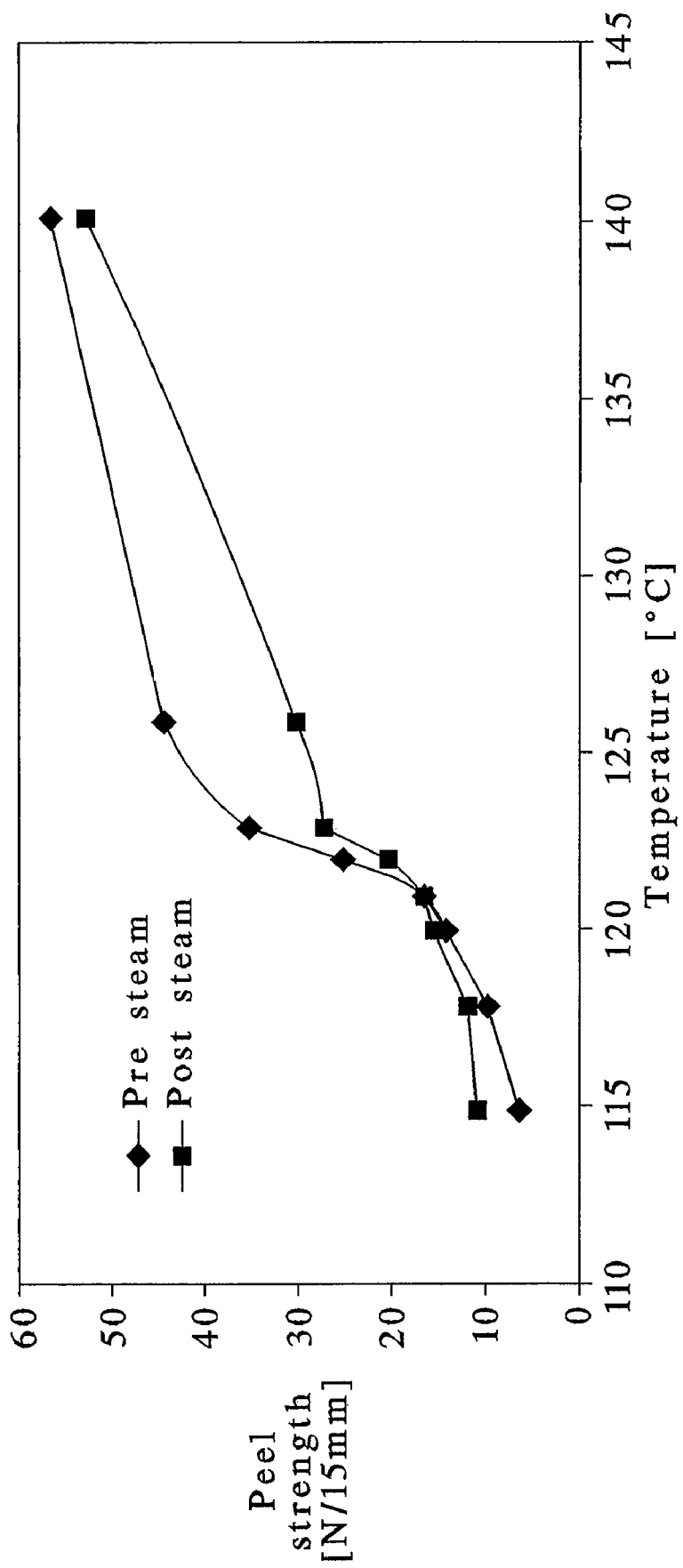
FIG. 9 illustrates graphically peel strength versus temperature of an embodiment of the seal layer of the present invention.

FIG. 9 illustrates graphically seal strength. The seal was done on a thermal sealer with a pressure of 2 MPa for a 3 second welding time. The seals were 200 mm long and 4 mm wide. The strength measurements were performed on an Instron tensile machine on 15 mm wide strips cut perpendicular to the seal.

The conclusions drawn from the data for the above four examples include:
1. All the tested formulations have peelable properties;
2. The addition of EVA increases the peelable value, i.e., the amount of force required to open the seal;
3. It appears that the addition of EVA decreases the strength of the permanent seal, apparently due to lower adhesion on the tie layer; and
4. Compounding LLDPE instead of dry blending has strong influence on the strength value.

Figure 10:
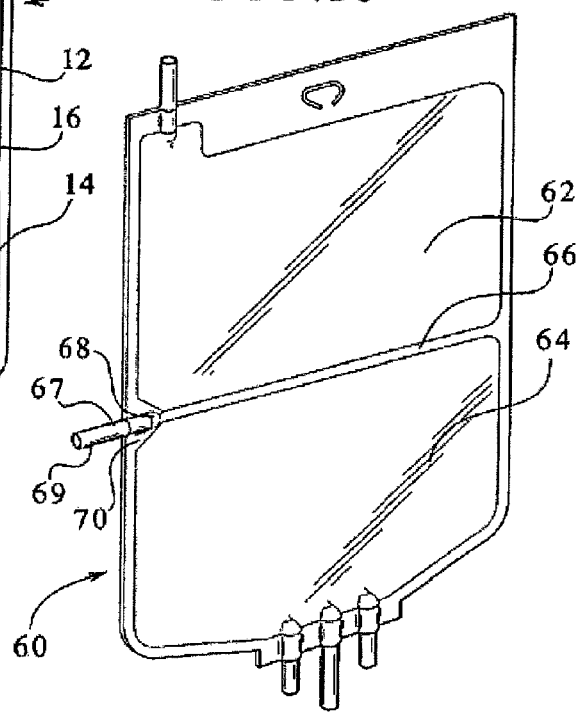
FIG. 10 illustrates another embodiment of the container of the present invention.

Referring now to FIG. 10, an embodiment of the present invention is illustrated. The container 60 in the embodiment illustrated is provided having two chambers 62 and 64 that are separated by a peel seal 66. However more than two chambers can be provided. As illustrated, the container 60 includes a port 67 that allows fluid communication outside of the container 60.

The container 60 includes an interior area 68 that is in fluid communication with an interior 69 of the port 67. The interior area 68 is defined in part by a peelable seal 70. Although it is not necessary, the peelable seal 70 can have a peel strength, in a preferred embodiment that is greater than the peel strength of the peelable seal 66. In use the first peelable seal 66 is separated, this allows solutions in chamber 62 and 64 to be mixed. When further pressure is applied, peelable seal 70 will open and the mixed solution becomes available for infusion to the patient through the port.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:
1. A container comprising:
at least one permanent side seal and defining at least two chambers having therebetween a peelable seal, the container comprising a film having:
an external layer including polypropylene that defines, at least in part, an outer surface of the container,
a core layer including polyamide, and
a sealant layer that defines, at least in part, an interior surface of the container, wherein the sealant layer has a bimodal thermal property and includes polypropylene, linear low density polyethylene and styrene-ethylene-butylene-styrene, wherein the sealant layer includes at least two grades of polypropylene each having a different melting point.

2. The container of claim 1, wherein the bimodal thermal behavior is such that a permanent seal is created at a temperature of at least 5° C. greater than the temperatures at which the peelable seal is created.

3. The container of claim 1 including a first area defined, in part, by a second peelable seal, the second peelable seal designed to separate upon an application of a sufficient fluid pressure.

4. The container of claim 1 including a port and an interior area in fluid communication with a portion of the port, the interior area being defined, at least in part, by a second peelable seal that segregates the interior area from at least one of the chambers.

5. A container comprising:
at least one permanent side seal and defining at least two chambers having therebetween a peelable seal, the container comprising a film having:
an external layer including polypropylene that defines, at least in part, an outer surface of the container,
a core layer including polyamide, and
a sealant layer that defines, at least in part, an interior surface of the container, wherein the sealant layer has a bimodal thermal property and includes polypropylene, linear low density polyethylene and styrene-ethylene-butylene-styrene, wherein the container includes a first area defined, in part, by a second peelable seal that is located in juxtaposition to a side of the container, the second peelable seal being designed to separate upon an application of a sufficient fluid pressure.

6. The container of claim 5, wherein the first area is coupled to a tube.

* * * * *